(12) United States Patent
Racey et al.

(10) Patent No.: US 9,446,073 B2
(45) Date of Patent: Sep. 20, 2016

(54) NON-LINEAGE COMMITTED PRECURSOR CELLS FROM THE DENTAL PAPILLARY TISSUE OF TEETH

(75) Inventors: Gary Racey, Worthington, OH (US); Russell Bowermaster, Dublin, OH (US); Thomas Bob, Powell, OH (US)

(73) Assignee: BIODONTOS, LLC, Dublin, OH (US)

( * ) Notice: Subject to any disclaimer, the term of this patent is extended or adjusted under 35 U.S.C. 154(b) by 1328 days.

(21) Appl. No.: 12/511,210

(22) Filed: Jul. 29, 2009

(65) Prior Publication Data

US 2009/0291496 A1    Nov. 26, 2009

Related U.S. Application Data

(63) Continuation-in-part of application No. 12/360,397, filed on Jan. 27, 2009, now abandoned, which is a continuation of application No. 11/417,719, filed on May 4, 2006, now abandoned.

(60) Provisional application No. 61/085,614, filed on Aug. 1, 2008.

(51) Int. Cl.
| | |
|---|---|
| *A61K 35/12* | (2015.01) |
| *C12N 5/074* | (2010.01) |
| *C12N 5/0797* | (2010.01) |
| *C12N 5/077* | (2010.01) |

(52) U.S. Cl.
CPC .............. *A61K 35/12* (2013.01); *C12N 5/0607* (2013.01); *C12N 5/0623* (2013.01); *C12N 5/0654* (2013.01); *C12N 2500/25* (2013.01); *C12N 2501/11* (2013.01); *C12N 2501/115* (2013.01); *C12N 2501/13* (2013.01); *C12N 2533/52* (2013.01); *C12N 2533/54* (2013.01)

(58) Field of Classification Search
None
See application file for complete search history.

(56) References Cited

U.S. PATENT DOCUMENTS

| | | |
|---|---|---|
| 5,690,926 A | 11/1997 | Hogan |
| 2007/0026520 A1 | 2/2007 | Kelly et al. |
| 2007/0160584 A1 | 7/2007 | Ueda et al. |
| 2007/0258957 A1 | 11/2007 | Bowermaster et al. |

FOREIGN PATENT DOCUMENTS

JP      2006238875      9/2006

OTHER PUBLICATIONS

Glycosan Biosystems (Stem cell culture, pp. 1-5, 2007).*
Thompson et al (J Anat 212, 72-80, Jan. 2008—Talk 7, p. 74).*
Techawattanawisal et al (BBRC 357: 917-923, 2007).*
Zipori (Curr Stem Cell Res Ther 1: 95-102, 2006) abstract.*
Degistirici et al (Tissue eng Part A 14: 317-330 2008).*
Kollar et al., The Influence of the Dental Papilla on the Development of Tooth Shape in Embryonic Mouse Tooth Germs. J. Embryo Exp. Morph, Feb. 1969, vol. 21, No. 1, pp. 131-48 (p. 132, "Materials and Methods," Plate 1, Fig. D).
Matsummura et al., Ameloblast-lineage Cells of Rat Tooth Germs Proliferate and Scatter in Response to Hepatocyte Growth Fctor in Culture. Int J Dev.Biol, 1998, vol. 42, pp. 1137-1142; p. 1141, Fig 6.
Shi et al., Perivascular Niche of Postnatal Mesenchymal Stem Cells in Human Bone Marrow and Dental Pulp. Journal of Bone and Mineral Research, 2003, vol. 18, No. 4, pp. 696-704; p. 697, left col. para 2; p. 699, left col, para 2, Fig 2.
Bidder et al., Reciprocal Temporospatial Patterns of Msx2 and Osteocalcin Gene Expression During Murine Odontogenesis. Journal of Bone and Mineral Research, 1998, vol. 13, No. 4, pp. 609-619; Abstract.
Sonoyama et al., Mesenchymal Stem Cell-Mediated Functional Tooth Regeneration in Swine, PLoS One, 2006, vol. 1, No. 1, e79, pp. 1-8; p. 3, Fig 2G.
Chai et al., Fate of the Mammalian Cranial Neural Crest During Tooth and Mandibular Morphogenesis. Development, 2000, vol. 127, pp. 1671-1679; Abstract.
International Search Report mailed Oct. 23, 2009 relating to corresponding PCT application No. PCT/US09/52058, filed Jul. 29, 2009.

\* cited by examiner

*Primary Examiner* — Daniel E Kolker
*Assistant Examiner* — Aditi Dutt
(74) *Attorney, Agent, or Firm* — Maginot, Moore & Beck, LLP

(57) ABSTRACT

Multipotent cranial neural crest stem cells and non-lineage committed precursor cells are described. The neural crest cells are capable of self-renewal, of being cultured into clonal spheroids including neurospheres, and of differentiation into neurons or other neuroepithelial cells. The non-lineage committed precursors are capable of differentiation into neurons, astrocytes and oligodendrocytes, and are capable of de-differentiation into induced pluripotent stem cells (iPSCs). Methods of obtaining, generating, isolating and culturing cranial neural crest stem cells and non-lineage committed precursor cells are also disclosed, including methods of providing a substantially pure in vitro cell culture consisting essentially of stem cells capable of multipotent differentiation and de-differentiation to a pluripotent state, which may be used for medical research or preserved for future therapeutic use by their autologous donor or a heterologous recipient.

10 Claims, No Drawings

NON-LINEAGE COMMITTED PRECURSOR CELLS FROM THE DENTAL PAPILLARY TISSUE OF TEETH

CROSS-REFERENCE TO RELATED APPLICATIONS

The present application claims priority to provisional application, No. 61/085,614, filed on Aug. 1, 2008, which claims priority to co-pending utility application Ser. No. 12/360,397, filed on Jan. 27, 2009, entitled "Method for Obtaining and Storing Multipotent Stem Cells", which is a continuation of, and claims priority to abandoned utility application Ser. No. 11/417,719 filed on May 4, 2006, in the name of the same inventors, which further claims priority to provisional application No. 60/668,183, filed on May 15, 2005. The disclosures of both application Ser. Nos. 12/360, 397 and 11/417,719 are incorporated herein by reference.

BACKGROUND

This invention relates to a method for identifying and in vitro sorting undifferentiated stem cells derived from migrating cranial neural crest (CNC) or from paraxial mesoderm of the first branchial arch. This invention also relates to the isolation, culture, proliferation, preservation and therapeutic use of these cells and their progeny.

Development of the mammalian nervous system (NS) begins in the early stages of fetal development and continues into the early post-natal period. Neural stem cells give rise to daughter stem cells and to neuroblasts and glioblasts. The mature mammalian nervous system is composed of neuronal cells (neurons and their axons), and of glial cells (astrocytes and oligodendrocytes). Neurons, the functional unit of the NS, are responsible for forming axonal connections with other neurons and with other functional end units (end organ sensory receptors, motor end plates, etc.)—they are the communicating cells of the NS. Astrocytes and oligodendrocytes provide a supportive role for optimal neuronal function.

Cells derived from neural tube give rise to the neurons and glia of the central nervous system (CNS) while cells derived from neural crest give rise to the peripheral nervous system (PNS). The neural crest also secretes nerve growth factor (NGF) which stimulates the development of neuronal axons throughout the NS.

Neurogenesis occurs primarily in two waves—a pre-natal wave during which most of the neurons are formed and an early post-natal wave during which most of the astrocytes and oligodendrocytes develop. The formation of neurons occurs in the fetal period and is completed by the early post-natal period. By the late post-natal period, the CNS has its full complement of nerve cells. Unlike other tissues, differentiated cells of the adult mammalian CNS demonstrate little ability to generate new nerve cells. While it is believed there is a slow or limited turnover of astrocytes and that progenitor cells for oligodendrocytes exist, the regeneration of new neurons is limited, particularly in adult primates. This limited ability of the CNS to produce new neurons is thought to be an advantage for long-term memory retention and for learned motor/sensory reflexes but it is a distinct disadvantage when the need to replace lost neurons or glial cells arises due to traumatic injury, neurological disease, or degenerative changes.

Growth-factor responsive cells from pre-natal and post-natal CNS exhibiting neural stem cell characteristics in vitro were isolated in the early 1990's (Reynolds, B. A. et. al., "Generations of neurons and astrocytes from isolated cells of the adult mammalian central nervous system," Science 255:1707-1710 (1992)). The location of a small quantity of neural stem cells capable of differentiating into neurons and glia has been identified in the post-natal brain (Lois, S. et. al., "Proliferating subventricular zone cells in the adult mammalian forebrain can differentiate into neurons and glia," Proc. Natl. Acad. Sci. USA, 90:2074-2077 (1993); Morshead, C. M. et. al., "Neural stem cells in the adult mammalian forebrain: a relatively quiescent subpopulation of subependymal cells," Neuron, 13(5): 1071-1082 (1994)). These studies have opened the door to an emerging area of neurobiological research, namely repair based on the generation of new cells within the NS.

Development of the mammalian dentition, dentinogenesis, begins in the early stages of fetal development and continues well beyond the early post-natal period. Tooth formation reflects a complex sequence of epithelial-mesenchymal interactions occurring between enamel organ epithelium (EOE) cells, derived from ectoderm, and cranial neural crest (CNC) and non-cranial neural crest (non-CNC), derived from mesoderm located within the first branchial arch. In addition to participating in tooth development, migrating cranial neural crest (CNC) cells also contribute to the central and peripheral nervous systems through development of the cranial nerves, the eye (and its associated muscles), and other structures.

A two-component genetic marking system has been utilized during craniofacial development to systematically analyze the migration and differentiation of CNC-derived ectomesenchyme from early embryogenesis onward. See, Chai, Y. et. al., "Fate of the mammalian cranial neural crest during tooth and mandibular morphogenesis," Development 127: 1671-1679 (2000). As described in Chai, at the initiation of tooth development (dental lamina stage, around 6-8 weeks in utero), the underlying mesenchyme within the maxillary and mandibular processes of the first branchial arch is composed almost entirely of migrating CNC-derived mesenchyme. As each individual tooth germ progresses from toothbud to cap stage, its CNC-derived mesenchyme begins to concentrate near remnants of the enamel organ epithelium (EOE), the structure responsible for enamel formation, while the remaining mesenchyme within the dental sac and dental papilla begins to demonstrate a mixture of CNC-derived mesenchyme and non-CNC-derived, or paraxial mesenchyme. Therefore, mesenchyme that will eventually form the mature dental pulp is populated by two lineages: CNC-derived mesenchyme and non-CNC-derived paraxial mesenchyme. CNC-derived mesenchyme concentrates in a circle of pulp tissue at the periphery of each developing tooth root adjacent to the epithelial root sheath and epithelial diaphragm, known as the "dental papillary ring" or "dental papillary annulus.". This area of the of the developing pulp, adjacent to ectodermal structures derived from enamel organ epithelium (EOE), attracts a higher concentration of CNC-derived undifferentiated cells while the central core of the developing pulp is populated with a higher concentration of paraxial (non-CNC-derived) mesenchyme.

Until apical closure of the developing tooth root occurs, developing dental pulp is properly termed "dental papilla," the mesenchymal structure which gives rise to the dental pulp and to the tooth's dentin. Only following apical closure is the term "dental pulp" properly applied. Therefore, dental pulp exists only after it is fully enclosed by dentin, also derived from dental papilla. For the proposes of this invention, "dental papillary annulus" or "dental papillary ring" refers to that portion of the developing pulp tissue at the periphery of each developing tooth root that is adjacent to the epithelial root sheath and epithelial diaphragm regardless of whether the term dental pulp or dental papilla is used to refer to the developing pulpal tissue.

Nervous system disorders include neurodegenerative diseases, injuries, tumors, and a large number of central nervous system (CNS) dysfunctions. While not limited to the elderly, neurodegenerative diseases have gained increasing attention because of their occurrence in an expanding elderly population, which is at greater risk. Cerebral Palsy, Multiple Sclerosis, Amyotrophic Lateralizing Sclerosis, Epilepsy, and diseases such as Alzheimer's disease, Parkinson's disease, Huntington's disease, have all been linked to the degeneration of neural cells in particular locations of the central nervous system, leading to the inability of these regions to function normally. CNS injuries and tumors often result in the loss of neural cells, inappropriate function of the affected region, and a subsequent constellation of sensory, motor or behavioral abnormalities. Other CNS dysfunctions which affect a large number of people are not characterized by a loss of neural cells but by the abnormal function of existing cells due to inappropriate neuronal function or to the abnormal synthesis, release or processing of neurotransmitters resulting in disorders such as autism, depression, neurosis and psychosis.

In the case of injuries and tumors, treatment for CNS disorders has primarily been interventional. In the case of neurodegenerative diseases and CNS dysfunction, treatment has primarily been pharmacologic with administration of agents designed to normalize function. Pharmacological therapy is limited by certain inherent difficulties including transportation of the drug across the blood-brain barrier, acquired drug tolerance, and drug side-effects. It would be advantageous to have a reliable, post-natal source of neural cells available at least for the study of CNS dysfunction, and more preferably for drug development and screening, as well as for regenerative medicine and tissue engineering.

SUMMARY

One objective of the present invention, therefore, is to provide a reliable source of undifferentiated neural cells which can be acquired from migrating cranial neural crest within the dental papillary annulus of developing teeth, i.e., developing third molars (wisdom teeth) commonly removed for a variety of dental indications (e.g., impaction, arch length deficiency, crowded dentition, orthodontic interference, etc.). These teeth can also be banked for their donor's future use instead of being discarded as a biohazardous waste material, as is the current practice.

Another objective is to provide a method for the in vitro cryopreservation, vitrification, lyophilization or other long-term storage (banking) of undifferentiated neural stem cells for use by their host (donor) or by other heterologous recipients. A further objective is to provide a method for the in vitro proliferation of undifferentiated neural stem cells to produce for transplantation significant numbers of neural precursor cells that are capable of differentiation into neurons, astrocytes and oligodendrocytes.

Yet another objective of the present invention is to provide a method of generating significant numbers of normal neural cells for the purpose of developing and screening putative pharmaceutical agents, therapeutic mechanisms, or regenerative and tissue engineering mechanisms which target the nervous system; and for developing models of nervous system development, function and dysfunction. An additional objective is to provide a method, or methods, for inducing undifferentiated or differentiated neural cells already present within the CNS to proliferate in vivo during dysfunction, thereby developing therapies which can eventually avert the need for neurotransplantation.

Thus, in one embodiment, the invention provides a method for acquiring dental papillary annulus from the pulp of any developing tooth harvested from a human, primate, or other mammal and then isolating that portion of the developing dental pulp that interfaces with derivatives of the enamel organ epithelium (EOE), the epithelial root sheath and the epithelial diaphragm, which remain within the tooth's developing root.

Another embodiment contemplates a method for the in vitro sorting of undifferentiated neural cells derived from migrating cranial neural crest concentrated in the dental papillary annulus of developing teeth. This method may comprise the steps of: (a) transferring the dental papillary annulus and other associated tooth structures in an osmotically-balanced preservative solution from a dental office, clinic or surgery to a laboratory without clinically significant loss of viable cells; (b) creating an isolated composition of the dental papillary annulus in a culture medium and/or media containing appropriate growth factors; (c) marking the composition's undifferentiated cells with surface and/or intracellular neural stem cell markers; (d) sorting the marked neural stem cells by FACS or other appropriate cell-sorting techniques and placing them, in pure culture, in a growth or preservative medium; and (e) generating a large quantity of undifferentiated neural stem cells by expansion. In one particular embodiment, a pure culture of undifferentiated neural stem cells is preserved, such as by cryopreservation, vitrification or lyophilization, for subsequent use by their donor or by another heterologous recipient.

The invention also provides for the proliferation and/or differentiation of undifferentiated neural cells in vitro for the purpose of in vivo transplantation of neural stem cells or their progeny into a human, primate, or other mammal for the treatment of neurodegeneration, disease, or trauma.

Another feature resides in the transfection of neural stem cells and their progeny with vectors which can express the gene for growth factors, growth factor receptors, peptide neurotransmitters, and enzymes involved in the synthesis of neurotransmitters, including amino acids, biogenic amines and neuropeptides; and for the transplantation of transfected cells into regions of neurodegeneration, disease, or trauma.

The invention also provides for generating a large number of undifferentiated neural stem cells for the purpose of neurological research and for the purpose of screening potential therapies, pharmaceuticals or other mechanisms targeting the nervous system during development, normal function, or disease.

DESCRIPTION OF THE PREFERRED EMBODIMENTS

For the purposes of promoting an understanding of the principles of the invention, reference will now be made to the embodiments illustrated in the drawings and described in the following written specification. It is understood that no limitation to the scope of the invention is thereby intended. It is further understood that the present invention includes any alterations and modifications to the illustrated embodiments and includes further applications of the principles of the invention as would normally occur to one skilled in the art to which this invention pertains.

Surface and intracellular marking of undifferentiated cells obtained from the dental papillary annulus can document the presence of undifferentiated neural stem cells that mark positive for one or more of the following markers: neuronal stem cell adhesion molecules CD56 (N-CAM) and CD133, alpha4-integrin (CD49d), platelet-derived growth factor receptor alpha (PDGFR$_{alpha}$) and nestin.sup. The undifferentiated cells may also mark positive for vimentin and/or noggin. These undifferentiated neural stem cells also mark negative for at least one of a group that includes: CD34; CD40; CD45; CD117; STRO-1; and MART-1.

Once tagged, these cells can be sorted by existing fluorescent-activated cell-storing (FACS) technology, placed in pure culture, and grown or preserved for future use. These cells can be marked, identified and sorted, isolated for growth in pure culture, and stored cryogenically, in vitrification or by lyophilization for future use by their donor or by a histo-compatible heterologous recipient. They can also be used in the study and therapeutic management of neurological disease to address one or more of the neurological conditions described above.

The present invention contemplates methods for acquiring the dental papillary annulus of any developing tooth. In one embodiment, the process comprises the steps of: (a) removing a selected developing tooth or teeth from a child or young adult; (b) transporting the tooth (teeth) in an osmotically-balanced preservative solution with or without an antibiotic/antifungal additive; (c) curetting the developing dental pulp from the tooth; (d) isolating the dental papillary annulus from the developing pulp with a scalpel, microtome or other similar device; and (e) placing the isolated dental papillary annulus in a culture or growth or preservative medium. Once isolated, the cell surfaces or intracellular substances are marked with one or more of the following neural stem cell markers as needed to identify cells derived from migrating cranial neural crest: neural stem cell adhesion molecule CD56 (NCAM), CD 133, CD49 (alpha4-integrin), platelet-derived growth factor receptor alpha (PDGFR$_{alpha}$) and nestin. The neural stem cells derived from migrating cranial neural crest are then sorted utilizing fluorescent assisted cell-sorting (FACS) or other appropriate cell sorting techniques for the purpose of acquiring a pure culture. Once the pure culture has been obtained, the next step is to induce undifferentiated (pluripotent) neural stem cells derived from migrating cranial neural crest to proliferate in vitro to generate large numbers of cells capable of differentiating into neurons, astrocytes, and oligodendrocytes.

The induction, proliferation and differentiation of pluripotent neural stem cells may be done either by culturing undifferentiated cells in suspension or on a substrate onto which they can adhere. Clonal spheroids including neurospheres of the cultured cells, consist of undifferentiated neural cells that stain positive for nestin sup., lack differentiated neural cells that do not stain positive for nestin sup. and stain negative for differentiated neural cell and neurofilament markers (e.g., neurofilament (NF) sup.-, etc.).

The culture medium may consist of neural growth factor or a combination of growth factors selected from a group consisting of platelet derived growth factor alpha (PDGF$_{alpha}$), epidermal growth factor, acidic fibroblastic growth factor, basic fibroblastic growth factor, transforming growth factor, amphiregulin, thyrotropin releasing hormone, insulin-like growth factor and the like. As used herein, "growth factor" refers to any protein, peptide or other molecule having a growth, proliferative, differentiative, or other trophic effect on neural stem cells derived from migrating cranial neural crest.

The resulting undifferentiated neural stem cells derived from migrating cranial neural crest obtained from the dental papillary annulus may be preserved by cryopreservation, tissue vitrification, or lyophilization, or by any other suitable means for subsequent use by their host (donor) or by a heterologous recipient.

As a further alternative, proliferation and differentiation can be induced in the host by: (1) in vitro proliferation and differentiation, then neurotransplantation into the host; or (2) in vitro genetic, pharmaceutical, or regenerative programming to induce in vivo proliferation and differentiation of in situ neural stem cells during dysfunction.

The present invention contemplates an in vivo cell culture or composition that is isolated from the dental papillary annulus of a developing tooth. The cell culture includes undifferentiated cells, clonal spheroids, including neurospheres, and growth medium, wherein the neurospheres include undifferentiated neural cells that mark positive for neuronal cell adhesion molecule (N-CAM+, CD56+) and CD133+, mark positive for at least one of the group including alpha4-integrin (CD49d+), platelet-derived growth factor receptor alpha (PDGFR$_{alpha}$), nestin+, vimentin+ and/or noggin+, and further mark negative for at least one of the group including CD40−, CD45−, CD117− and/or MART-1−.

The cell culture is preferably composed of cranial neural crest (CNC)-derived undifferentiated cells. The cells may be further obtained from the cementum, periodontium, dental alveolar bone, mandible, maxilla or other facial bone, including their respective periosteum or marrow. In accordance with the present disclosure, the undifferentiated cells are obtained from any mammal, primate or human.

In another embodiment, a method of producing a substantially pure in vitro cell culture comprises the steps of: (a) providing dental tissue; (b) dissecting the dental tissue to isolate its dental papillary annulus; and (c) culturing the annular tissue as adherent explants on collagen-coated and/or fibronectin-coated culture substrates to isolate non-lineage committed precursor cells (n-LCPs). The dissecting step may include dissecting that portion of the developing dental epithelial tissue associated with tooth development. The dissecting step may also include dissection of that portion of the developing dental tissue which interfaces with derivatives of enamel organ epithelium, epithelial diaphragm, Hertwig's epithelial root sheath, or epithelial rests of Malassez.

The isolated n-LCPs are then cultured as this n-LCP population is expanded as adherent cells by sub-culture or other suitable means. This cell culture may include, in addition to the n-LCP population, some or all of the following components: collagen, fibronectin, alpha-modified MEM or other culture medium, insulin, transferring, selenium, essential fatty acids, growth factors including fibroblastic growth factors or epidermal growth factors, and neurotropins. The n-LCP population expanded as adherent cells are preferably capable of adhering to a substratum comprised of collagen, fibronectin or other substantially similar substrates.

In accordance with this method, the yield of isolated n-LCPs is at least $3\times10^5$ cells per explant culture within three (3) to four (4) days after onset of emigration. Further, the n-LSP cell population has a purity level greater than 66.6% without the need to further purify the cell culture. In certain optimal embodiments, the n-LSP cell population has a purity level of at least 80% without the need to further purify the cell culture.

The method further contemplates isolating the n-LCP cell population using one or more of the following markers: Nestin, PDGFR$_{alpha}$, CD49d (alpha4-integrin), CD56 (N-CAM), CD133. A positive expression of any of these markers is indicative of a non-lineage committed precursor cell, along with the positive expression of one or more of the following marker genes: Sox2, Sox9, Sox10, Snail1, Snail2, D1x6, Pcbp4, Msx2, HIfx, Thip1, Vars2, Myo10, 270094K13Rik, Ets1, Pygo2, Adam12, 5730449L18Rik, Rex3, Vdac1, AU041707, Pfn1, Crmp1, Ubc4b; and combinations thereof. The n-LCP cell population is spindle-shaped or stellate-shaped, and exhibits a high degree of motility and plasticity. Moreover, the adherent cells obtained according to this method are multipotent and are capable of differentiation into neural crest-derived and cranial neural crest-derived cells, including; dental papilla and its derivatives, dental follicle and its derivatives, clonal spheroids including neurospheres consisting essentially of undifferentiated neural cells, cardiospheres consisting essentially of undifferentiated cardiac cells, differentiated neurons and glial cells, myocytes, cardiomyocytes, smooth muscle cells, chondrocytes, osteocytes, adipocytes, dermacytes, melanocytes, dermal papilla, epidermal bulge and related dermal cells, mesenchymal stem cells and their derivatives. The adherent cells produced herein may also be pre-dental lineage committed and capable of de-differentiation or genetic re-programming to a pluripotent embryonic stem cell state.

The foregoing method may be applied to any cell or tissue, whether embryonic, pre-natal or post-natal, that is a precursor cell or tissue of the dental papillary annulus or derivatives thereof, which are capable of being de-differentiated or re-programmed to a pluripotent embryonic stem cell state in the manner of an induced pluripotent stem cell (iPSC).

The present invention further contemplates a cell culture of a substantially pure population of pre-dental non-lineage committed (n-LCPs) obtained by the method described. The n-LCPs may be human cells or cells from any mammal, whether embryonic, pre-natal or post-natal. The cells may be used, created or bred for medical, dental, therapeutic or treatment purposes, or research purposes. In a preferred application, the n-LCPs are preserved by known techniques, such as cryopreservation, vitrification or lyophilization for subsequent use by their donor or by a heterologous recipient.

The cell cultures of the present invention include n-LCP cells that: (i) are spindle or stellate shaped, (ii) are motile, (iii) are numerous, (iv) are highly proliferative, (v) have a purity level of greater than 66.6%, (vi) are multipotent, and (vii) are capable of undergoing differentiation to mesenchymal and neural crest derivatives. The n-LCP cells of the cell culture may also be (viii) capable of undergoing de-differentiation or re-programming to a pluripotent embryonic state in the manner of an induced pluripotent stem sell (iPSC); (ix) characterized by the positive expression of one or more of the following markers: Nestin, PDGFR$_{alpha}$, CD49d (alpha4-integrin), CD56 (N-CAM), CD133, and characterized by the positive expression of one or more of the following marker genes: Sox2, Sox9, Sox10, Snail1, Snail2, D1x6, Pcbp4, Msx2, HIfx, Thip1, Vars2, Myo10, 270094K13Rik, Ets1, Pygo2, Adam12, 5730449L18Rik, Rex3, Vdac1, AU041707, Pfn1, Crmp1, Ubc4b; and combinations thereof, and (x) further characterized by the negative expression of one or more of the following markers: CD34, CD40, CD45, CD117, STRO-1 and MART-1.

In another embodiment, the cell cultures of the present invention comprise a substantially pure population of non-lineage committed precursor cells (n-LCPs) which are: (i) derived from dental papillary annulus of developing teeth, (ii) have a purity level of greater than 66.6%, (iii) are multipotent, (iv) are capable of undergoing directed differentiation to mesenchymal and neural crest derivatives, (v) are capable of undergoing de-differentiation or re-programming to a pluripotent embryonic state in the manner of an induced pluripotent stem sell (iPSC); (vi) are characterized by the positive expression of one or more of the following markers: Nestin, PDGFR$_{alpha}$, CD49d (alpha4-integrin), CD56 (N-CAM), CD133; and are characterized by the positive expression of one or more of the following marker genes: Sox2, Sox9, Sox10, Snail1, Snail2, D1x6, Pcbp4, Msx2, HIfx, Thip1, Vars2, Myo10, 270094K13Rik, Ets1, Pygo2, Adam12, 5730449L18Rik, Rex3, Vdac1, AU041707, Pfn1, Crmp1, Ubc4b; and combinations thereof, and (vii) are further characterized by the negative expression of one or more of the following markers: CD34, CD40, CD45, CD117, STRO-1 and MART-1.

The invention in one aspect thus provides an isolated, pure, homogeneous population of mammalian cranial neural crest stem cells derived from migrating cranial neural crest associated with the development of any tooth. In another aspect, the invention provides an isolated, pure, homogeneous population of non-lineage committed precursor cells derived from migrating cranial neural crest associated with the development of any tooth.

While the invention has been illustrated and described in detail in the drawings and foregoing description, the same should be considered as illustrative and not restrictive in character. It is understood that only the preferred embodiments have been presented and that all changes, modifications and further applications that come within the spirit of the invention are desired to be protected.

What is claimed is:

1. A method of producing a substantially pure in vitro cell culture of non-lineage committed precursor cells (n-LCP) isolated from the dental papillary annulus of teeth in any stage of development, comprising:
   (a) providing dental tissue in any stage of development from a mammal;
   (b) dissecting the dental tissue to isolate its dental papillary annulus;
   (c) culturing the annular tissue as adherent explants on collagen-coated and/or fibronectin-coated culture substrates to isolate n-LCPs characterized by the positive expression of one or more of the following markers:
      i. Nestin, PDGFR$_{alpha}$, CD49d (alpha4-integrin), CD56 (N-CAM), CD133;
      ii. and further characterized by positive expression of one or more of the following marker genes: Sox2, Sox9, Sox10, Snail1, Snail2, D1x6, Pcbp4, Msx2, HIfx, Thip1, Vars2, Myo10, 270094K13Rik, Ets1, Pygo2, Adam12, 5730449L18Rik, Rex3, Vdac1, AU041707, Pfn1, Crmp1, Ubc4b; and
   (d) culturing one or more of the isolated n-LCPs as adherent cells under suitable conditions to obtain a substantially pure population; and
   (e) expanding one or more of the isolated n-LCP populations as adherent cells by sub-culture or other suitable means.

2. The method of claim 1 wherein the cell culture obtained in steps (d) and (e) include, in addition to the n-LCP population, some or all of the following components: collagen, fibronectin, alpha-modified MEM or other culture medium, insulin, transferrin, selenium, essential fatty acids, growth factors including fibroblastic growth factors or epidermal growth factors, and neurotropins.

3. The method of claim 1, wherein adherent cells of steps (d) and (e) are capable of adhering to a substratum comprised of collagen, fibronectin or other substantially similar substrates.

4. The method of claim 1, wherein step (c) yields isolated n-LCPs at least $3 \times 10^5$ cells per explant culture within three (3) to four (4) days after emigration of the annular tissue onto the substrates.

5. The method of claim 1, wherein the n-LCP cell population has a purity level greater than 66.6% without the need to further purify the cell culture.

6. The method of claim 5, wherein the n-LSP cell population has a purity level of at least 80% without the need to further purify the cell culture.

7. The method of claim 1, wherein the n-LCP cell population is spindle-shaped or stellate-shaped, and exhibits a high degree of motility and plasticity.

8. The method of claim 1, wherein the adherent cells obtained in step (e) are multipotent and are capable of differentiation into neural crest-derived and cranial neural crest-derived cells, including; dental papilla and its derivatives, dental follicle and its derivatives, dental follicle and its derivatives, clonal spheroids including neurospheres consisting essentially of undifferentiated neural cells, cardiospheres consisting essentially of undifferentiated cardiac cells, differentiated neurons and glial cells, myocytes, cardiomyocytes, smooth muscle cells, chondrocytes, osteocytes, adipocytes, dermacytes, melanocytes, dermal papilla, epidermal bulge and related dermal cells, mesenchymal stem cells and their derivatives.

9. The method of claim 1, wherein the dissecting step includes dissecting that portion of the developing dental epithelial tissue associated with tooth development.

10. The method of claim 9, wherein the dissecting step includes dissecting that portion of the developing dental tissue which interfaces with derivatives of enamel organ epithelium, epithelial diaphragm, Hertwig's epithelial root sheath, or epithelial rests of Malassez.

\* \* \* \* \*